(12) United States Patent
Hiraoka et al.

(10) Patent No.: US 8,030,090 B2
(45) Date of Patent: Oct. 4, 2011

(54) METHOD AND APPARATUS FOR SELECTIVELY SEVERING AND ANALYZING NON-COVALENT AND OTHER BONDS OF BIOLOGICAL MACROMOLECULES

(75) Inventors: Kenzo Hiraoka, Yamanashi (JP); Satoko Akashi, Kanagawa (JP); Atsushi Takamizawa, Yamanashi (JP); Jan Arne Sunner, Portsmouth (GB)

(73) Assignee: University of Yamanashi, Yamanashi (JP)

( * ) Notice: Subject to any disclaimer, the term of this patent is extended or adjusted under 35 U.S.C. 154(b) by 1357 days.

(21) Appl. No.: 11/596,769

(22) PCT Filed: May 17, 2005

(86) PCT No.: PCT/JP2005/009301
§ 371 (c)(1),
(2), (4) Date: Nov. 16, 2006

(87) PCT Pub. No.: WO2005/111594
PCT Pub. Date: Nov. 24, 2005

(65) Prior Publication Data
US 2009/0071815 A1    Mar. 19, 2009

(30) Foreign Application Priority Data

May 18, 2004  (JP) ................................ 2004-148323

(51) Int. Cl.
*G01N 24/00*  (2006.01)
(52) U.S. Cl. ........................................ 436/173; 436/164
(58) Field of Classification Search .................. None
See application file for complete search history.

(56) References Cited

FOREIGN PATENT DOCUMENTS

| | | |
|---|---|---|
| JP | 2003-157793 | 5/1993 |
| JP | 5-256837 | 8/1993 |
| JP | 10-48183 | 2/1998 |
| JP | 10-132788 | 5/1998 |
| JP | 2004-534354 | 11/2002 |
| JP | 2003-242925 | 8/2003 |
| JP | 2004-69501 | 3/2004 |
| JP | 2005-026159 | 1/2005 |
| WO | WO 03/102033 A2 | 12/2003 |

OTHER PUBLICATIONS

Takamizawa et al. "Selective dissociation of non-covalent bonds in biological molecules by laser spray", J. Mass Spectrom. 2004 v. 39, pp. 1053-1058.*
Leisner et al. "Infrared Laser Post-Ionization of Large Biomolecules from an IR-MALD(I) Plume", J Am Soc Mass Spectrom 2004, v. 15, pp. 934-941.*
"Activation Energies for Dissociation of Double Strand Oligonucleotide Anions: Evidence for Watson—Crick Base Pairing in Vacuo," Paul D. Schnier, John S. Klassen, Eric F. Strittmatter, and Evan R. Williams, J.Am. Chem. Soc., 1998, 120, 9605-9613.
Kenzo Hiraoka, "Laser spray: electric field-assisted matrix-assisted laser desorption/ionization", Journal of Mass Spectrometry, 2004, pp. 341-350, vol. 39.
Clifford H. Watson et al., "Laser Photodissociation of Gaseous Ions Formed by Laser Desorption", Analytical Chemistry, Apr. 15, 1987, pp. 1133-1138, vol. 59, No. 8.

* cited by examiner

*Primary Examiner* — Yelena G Gakh
(74) *Attorney, Agent, or Firm* — Dickstein Shapiro LLP

(57) ABSTRACT

A biological sample solution is ionized by electrospray and the sample solution is irradiated with an infrared laser beam to dissociate biological macromolecules into the constituents thereof. As a result, only non-covalent bonds of the biological macromolecules can be selectively severed and analyzed.

9 Claims, 8 Drawing Sheets

METHOD AND APPARATUS FOR SELECTIVELY SEVERING AND ANALYZING NON-COVALENT AND OTHER BONDS OF BIOLOGICAL MACROMOLECULES

TECHNICAL FIELD

This invention relates to a method and apparatus for selectively severing and analyzing non-covalent bond and other bonds of biological macromolecules.

BACKGROUND ART

In ion analyzing equipment such as a mass analyzer, it is necessary to ionize the sample that is to be analyzed. Accordingly, an ionization apparatus is provided as a preliminary stage of these ion analyzers.

The electrospray ionization (ESI) method is available as one ionization method used in an ion analyzer.

The electrospray ionization (ESI) method is in wide use as one method that has the ability to ionize biological macromolecules such as DNA and proteins. With the ESI method, DNA and proteins can be ionized gently and complexes comprising multiple DNA or proteins formed by non-covalent bonding also can be ionized as is. In view of this feature, the ESI method is being used in structural functional analysis of biological molecules.

Biological activity is governed by the interactions of a variety of biological molecules. Accordingly, although the overall molecular mass of a complex formed by the interaction of biological molecules is important information in terms of understanding biological phenomena, ascertaining the strength of this interaction also is vital.

In order to analyze by mass analysis the strength of interaction between molecules of complex ions produced by the ESI method, use generally is made of a method that combines the ESI method with collision-induced activation. This method is as follows: A complex comprising a plurality of biological molecule subunits is ionized by the ESI method and molecular-weight-related ions of the complex are observed. Next, the ions are introduced into a vacuum, the ions are accelerated by an electric field and made to collide with gas molecules in vacuo to bring about collision-induced activity, the complex is dissociated into each of the constituents that form the complex and the correlation between the imparted collision activation energy and binding strength is investigated.

In the case of a complex of a protein-low-molecular weight compound, such as an enzyme and coenzyme or a drug acceptor and drug, this method is such that only the non-covalent bonds are severed and the individual molecules are dissociated without causing dissociation of the protein and low-molecular weight compound, allowing the strength of the interaction to be studied.

However, in a case where electrostatic-interactions and hydrogen bonding are the prime causes of formation of the complex and the structure of the constituent molecules is not sufficiently stable, as in the case of a complex comprising double-stranded DNA and protein, there are instances where not only the non-covalent bonds but also weak covalent bonds are broken and measured together with these fragments if the above-described method is applied. For example, severance of the covalent bonds of the double-stranded DNA portion of the complex also occurs. The reason for this is that the collision activation energy is consumed by both the dissociation and fragmentation of the complex. Consequently, the spectra obtained are complicated and it is difficult to quantitatively analyze the strength of the interaction accurately using the ordinary ESI—collision activation method. For example, refer to the following literature:

Activation Energies for Dissociation of Double Strand Oligonucleotide Anions: Evidence of Watson-Crick Base Paring in Vacuo, Schnier P D, Klassen J S, Strittmatter E F and Williams E R JACS (1998) 120, 9605-9613.

One other problem in the ion analysis of biological macromolecules is that there are cases where the solution of the biological sample unavoidably contains a surface-active agent. For example, a surface-active agent is necessary in order to extract liposoluble protein. If the solution of the biological sample contains a surface-active agent, it will be difficult to vaporize and ionize the protein with the ESI method.

DISCLOSURE OF THE INVENTION

The present invention provides a method whereby only non-covalent bonds of a biological macromolecule can be selectively severed and analyzed.

The present invention further provides a method whereby various bonds that include non-covalent bonds of biological macromolecules are selectively severed and analyzed.

The present invention further provides a method through which the analysis of biological macromolecules such as proteins is possible regardless of the presence of a surface-active agent.

The present invention further provides an analyzing apparatus that is suited to the selective severance described above.

A method of analyzing biological macromolecules according to the present invention comprises introducing a solution containing a biological sample into a capillary, and irradiating the sample solution, which flows out of a tip of the capillary under an applied electric field with a first infrared laser beam, thereby causing the biological macromolecules to dissociate into their constituents in the solution; and introducing the dissociated constituent ions or biological macromolecular ions into a principal section of an analyzing apparatus. The dissociation of the biological macromolecules into its constituents also takes place in electrically charged droplets that have been produced. The principal section of the analyzing apparatus refers to a section that generates data for identifying the dissociated constituent ions or biological macromolecular ions. (In general, this principal section is referred to as an analyzer). The infrared laser beam has a wavelength of 10.6 μm, by way of example.

The sample solution that contains the biological macromolecules is sprayed from the tip of the capillary under an electric field by the electrospray method. Owing to irradiation with the first infrared laser beam, the complex comprising a plurality of biological molecules is decomposed into its constituents (subunit molecules) in the solution. The gaseous-phase ionization of the decomposed constituents is accelerated by the irradiation with the first infrared laser beam much more in comparison with the electrospray method. Further, only the non-covalent bonds of the complex are selectively severed by the irradiation with the infrared laser beam; other covalent bonds, etc., are not broken. Thus, the biological molecules that are the constituents of the complex are caused to dissociate from the complex without fragmentation, and the production of gaseous-phase ions is promoted. By introducing the ions to the principal section of the analyzer, therefore, highly sensitive detection of the complex and biological molecules and the analysis thereof become possible. Further, even if the solution of the biological sample contains a surface-active agent, the biological sample is readily vaporized and ionized by irradiation with the first infrared laser beam and therefore the analysis thereof is possible.

In a case where covalent bonds, etc., not severed by the infrared laser beam are to be severed, the complex or the constituents are irradiated with a second laser beam. The wavelength of the second laser beam should be decided in dependence upon the type, etc., of the bond to be severed.

Preferably, the biological sample is subjected to temperature control such as heating and cooling as necessary. Cooling makes it possible to handle a complex consisting of bonds that are very weak and difficult to measure under ordinary temperatures (e.g., room temperature).

Further, it may be arranged so as to vary the laser beam intensity and introduce the constituent ions, which have been produced at each laser beam intensity, into the principal section of the analyzing apparatus. Since there are instances where the constituent ions generated differ depending upon the intensity of the laser beam, this is useful in clarifying binding strength.

The method may include a step of introducing biological macromolecules, which have been ionized under no irradiation with the first infrared laser beam, into the principal section of the analyzer, and a step of introducing constituent ions, which have been produced under irradiation with the first infrared laser beam, into the principal section of the analyzing apparatus.

An analyzing apparatus according to the present invention comprises: a capillary for supplying a sample solution; means for forming an electric field in the vicinity of a tip of the capillary; means for adjusting temperature of droplets inside the capillary or sprayed from said capillary; a first infrared laser light source disposed so as to irradiate the vicinity of the tip of the capillary with an infrared laser beam; and means for introducing ions of the sample sprayed from the tip of the capillary, or constituent ions disassociated by irradiation with the infrared laser beam, to a principal section of the analyzing apparatus. The means for forming the electric field in the vicinity of the tip of the capillary and the means for adjusting the temperature take on various forms as illustrated in the embodiments described later. The means for introducing the ions of the sample or the disassociated constituent ions into the principal section of the analyzing apparatus may be an orifice provided with an ion introduction port of the analyzing apparatus.

Providing the second laser light source makes it possible to cleave bonds such as covalent bonds as well. Further, a monitor can be provided and the state of the spray of sample solution in the vicinity of capillary tip can be imaged. A variety of temperature adjusting devices and structures can be provided.

The present invention further provides a nano-laser spray apparatus.

BEST MODE FOR CARRYING OUT THE INVENTION

First Embodiment

Figure 1:
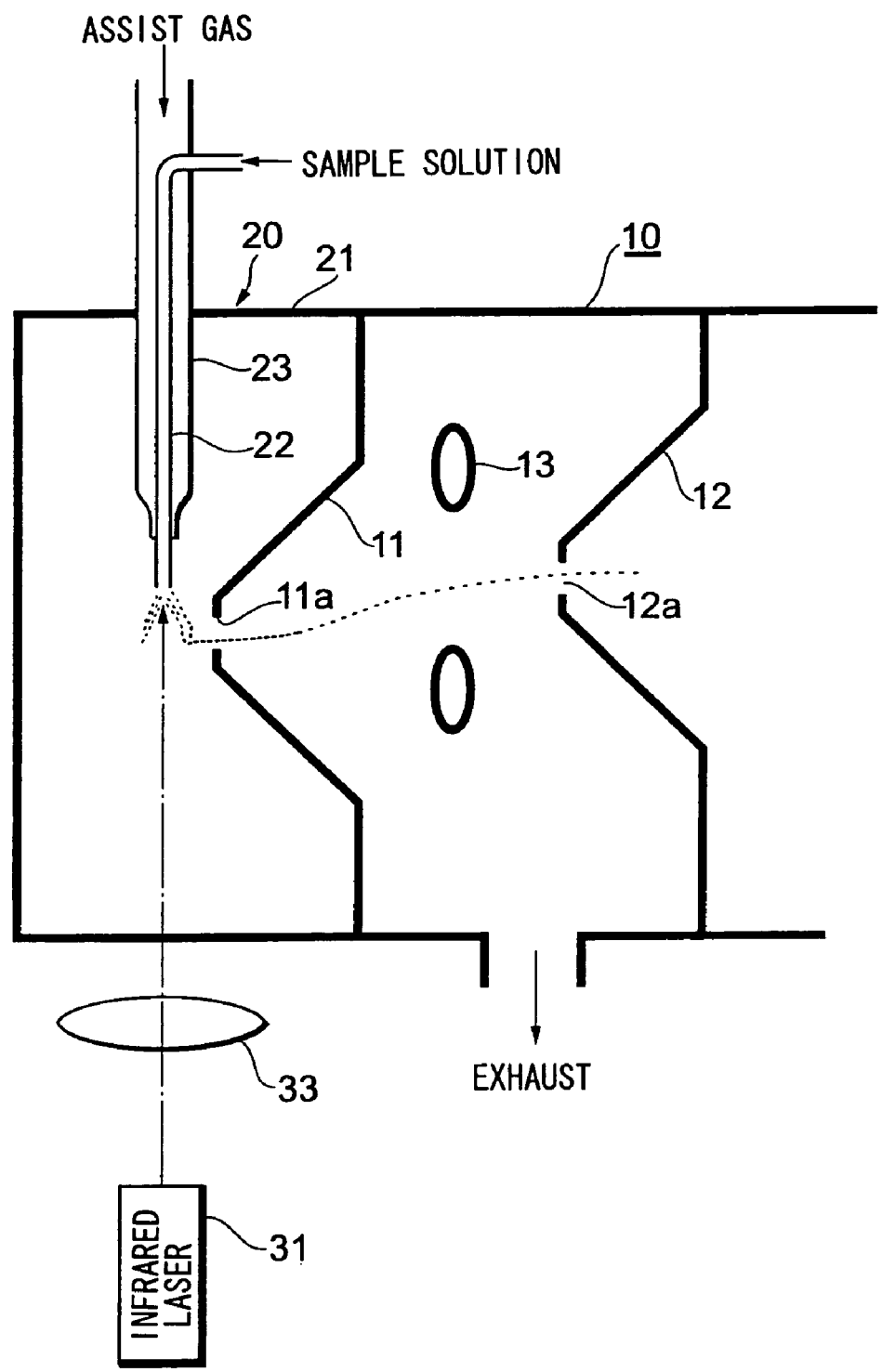
FIG. 1 is a structural view of an analyzing apparatus according to a first embodiment.

FIG. 1 illustrates the overall structure of an analyzing apparatus that includes a laser spray apparatus attached to a mass analyzer in the vicinity of an ion introduction port thereof.

A first orifice 11 provided with a miniscule hole 11a is attached to a mass analyzer 10 at the ion introduction port thereof. The miniscule hole 11a serves as the ion introduction port. The interior of the mass analyzer 10 is held in vacuum. A second orifice 12 provided with a miniscule hole 12a is provided deeper within the mass analyzer 10. A ring lens 13 is provided between the first orifice 11 and second orifice 12. Ions produced by a laser spray apparatus 20 pass through the miniscule hole 11a of the first orifice 11, are deflected by the lens 13, pass through the miniscule hole 12a of the second orifice 12 and are introduced to the interior of the mass analyzer 10.

A housing 21 of the laser spray apparatus 20 is attached to the vessel wall of the mass analyzer 10 so as to surround and cover the orifice 11. The space delimited by the housing 21 and orifice 11 is an ionization space. The interior of the ionization space may be at atmospheric pressure. Of course, the interior of the ionization space may be held in vacuum. The entirety of the mass analyzer 10 and laser spray apparatus 20 corresponds to the analyzing apparatus of the present invention. The mass analyzer 10 corresponds to the principal section of the analyzing apparatus according to the present invention.

A capillary 22 for supplying a biological sample solution that contains biological macromolecules and an outer tube 23 that surrounds the outside of the capillary 22 with the exception of the tip thereof are provided so as to penetrate the wall of the housing 21. The tip of the capillary 22 is situated in the vicinity of the miniscule hole 11a inside housing 21. The capillary 22 is guided to the outside from the outer tube 23 at the exterior of the housing 21. There is a gap (clearance) between the outer peripheral surface of the capillary 22 and the inner peripheral surface of the outer tube 23, and an assist gas ($N_2$ gas) for temperature adjustment (for cooling or for heating) is supplied through the gap (in a case where drying of the liquid sample is to be accelerated, an improved effect is obtained if the gas is dried). The end of the outer tube 23 is formed to have a tapered shape just short of the tip of the capillary 22 within the housing 21, and the diameter of the tube is thus reduced to narrow the gap. The assist gas that has been supplied to the gap is jetted into the ionization space from the end of the outer tube 23.

A positive or negative high voltage is applied to the vicinity of the tip of the capillary 22. The capillary 22 may be formed from a conductor and the high voltage may be applied to the capillary 22. Alternatively, if the capillary 22 is an insulator such as a glass tube, a metal membrane may be vapor-deposited on the outer peripheral surface of the capillary 22 and the high-voltage may be applied to this metal membrane. A conductive wire to which the high voltage is applied may also be inserted into the capillary 22. The high voltage may also be applied to the outer tube 23.

Thus, an electrospray apparatus is constructed by the capillary 22 and outer tube 23. In a case where the solution inside the capillary 22 is cooled by the assist gas ($N_2$ gas), this can also be referred to as a "cold spray". A cold spray makes it possible to analyze complexes having weak bonds.

An infrared laser device 31 is disposed outside the housing 21. The infrared laser device 31 emits an infrared laser beam having a wavelength of 10.6 μm. The laser beam is condensed by a lens 33 and enters the interior of the housing 21 through an opening in the housing 21 or through a window formed by a transparent body. The laser device 31 is disposed in such a manner that the emitted laser beam will be projected upon the tip of the capillary 22 along the axial direction of the capillary 22. It is also permissible to adopt an arrangement in which the laser device 31 is placed at the side of the capillary 22 and the emitted laser beam is projected upon the tip of the capillary 22 from a direction perpendicular to the axial direction of the capillary 22. In this case the tip of the capillary 22 is transparent to infrared light. A position slightly outward from the tip of the capillary 22 may be irradiated with the laser beam.

The biological sample solution is supplied from the capillary 22 to the tip thereof, and the solution is sprayed together with the assist gas from the tip of the capillary. At this time the biological sample is ionized in the state of a complex (biological macromolecules) comprising a plurality of biological molecules (constituents). By irradiating the complex-containing biological sample solution with the infrared laser beam in the vicinity of the tip of the capillary 22, the non-covalent bonds of the complex are selectively severed without severing the covalent bonds, and the complex is dissociated into the ions of its constituents. Ionization is promoted by irradiation with the infrared laser beam. The ions of the complex or the ions of the dissociated constituents are introduced into the mass analyzer 10 from the miniscule hole 11a of the orifice 11.

Figure 2:
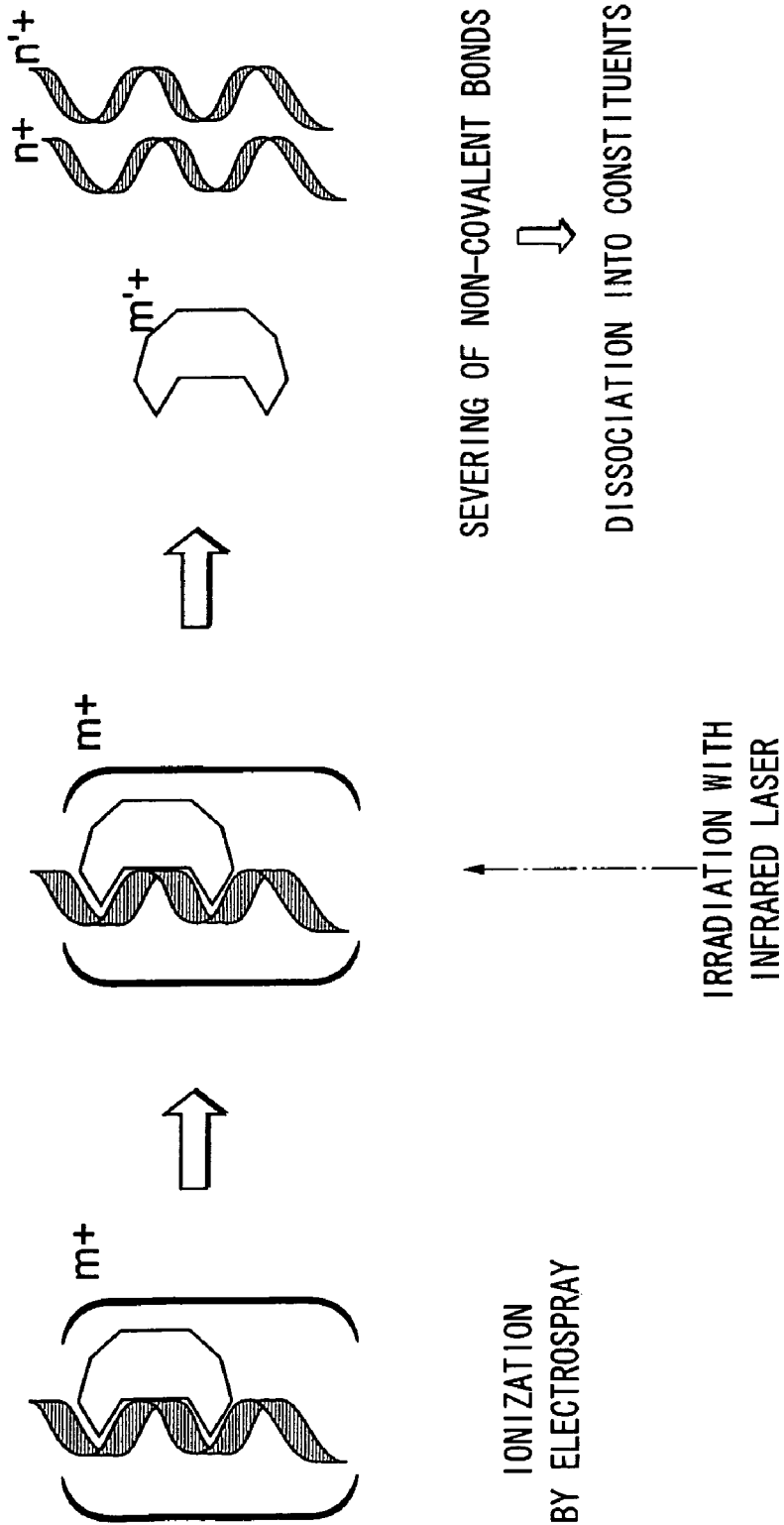
FIG. 2 illustrates an example in which biological macromolecules (a complex) are ionized by electrospray and then disassociated into their constituents by irradiation with an infrared laser.

As an illustration of one example, ions of a double-stranded DNA—protein complex in a sample are produced by electrospray, as depicted in FIG. 2. The ions of the complex are dissociated into a protein ion and two single-stranded DNA ions, with only the hydrogen bond (non-covalent bond) being severed by irradiation with the infrared laser beam. The single-stranded DNA ions are not decomposed at all by irradiation with the infrared laser beam. It should be noted that ionization and dissociation into constituents are illustrated in FIG. 2 as occurring in the order mentioned in order to facilitate understanding. In actuality, however, there are many cases where these occur simultaneously or where ionization takes place after the dissociation into constituents. The complex dissociates into constituents in solution (droplets) owing to irradiation with the infrared laser beam.

Figure 3:
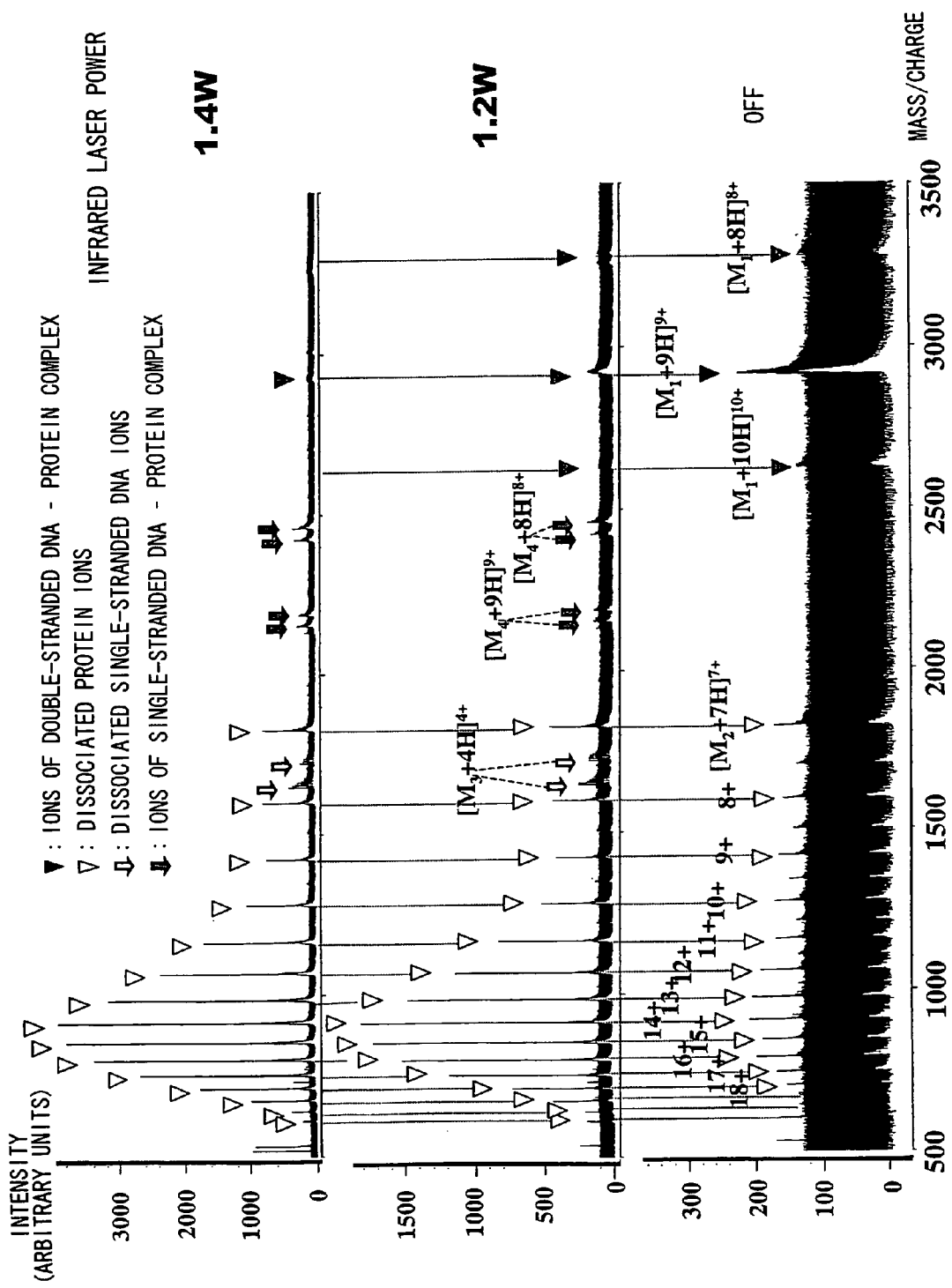
FIG. 3 illustrates mass spectra.

FIG. 3 illustrates mass spectra obtained when the power of the infrared laser beam is varied from zero (off) to 1.2 W and to 1.4 W.

When the intensity of the emitted infrared laser beam is raised, the dissociation of protein ion from the ions of the double-stranded DNA—protein complex proceeds; almost no complex ions are observed under laser irradiation at 1.4 W. Two single-stranded DNA ions are observed and absolutely no ions indicating severance of covalent bonds of DNA molecules are observed.

Thus, non-covalent bonds ascribable to hydrogen bonding or electrostatic interactions are severed selectively by irradiation with the infrared laser beam. Changing the intensity of the emitted laser beam makes it possible to perform analysis with regard to the strength of bonding due to electrostatic interaction between molecules or strength of hydrogen bonding.

The above-described method is applicable to many effective analyses, as will be set forth next.

In drug—DNA interactions or drug—protein interactions, not just DNA—protein complex interactions, there are many cases where a complex is formed with electrostatic interaction or hydrogen bonding being the prime cause. In particular, when drugs that will interact are screened from a plurality of candidate compounds in the drug discovery process, if use can be made of a method, such as mass analysis, that is applicable even in mixtures and exhibits a high throughput, this will be extremely effective since the time needed to narrow down compounds that are candidates for pharmaceuticals can be shortened. For example, ten types of candidate compounds having different molecular weights and doubled-stranded DNA, which is the target, are mixed, and the ions of the complex are detected first by the ESI method. At this stage a compound that is capable of forming a complex is ascertained from the ten types of candidate compounds judging from the molecular weights of the molecular-weight-related ions observed. Irradiation with an infrared laser beam is then performed and at this time the intensity of the emitted laser is varied to thereby analyze the manner in which the ions of the complex dissociate. The ease with which the complex ions dissociate can be ranked based upon the change in laser intensity.

Figure 4:
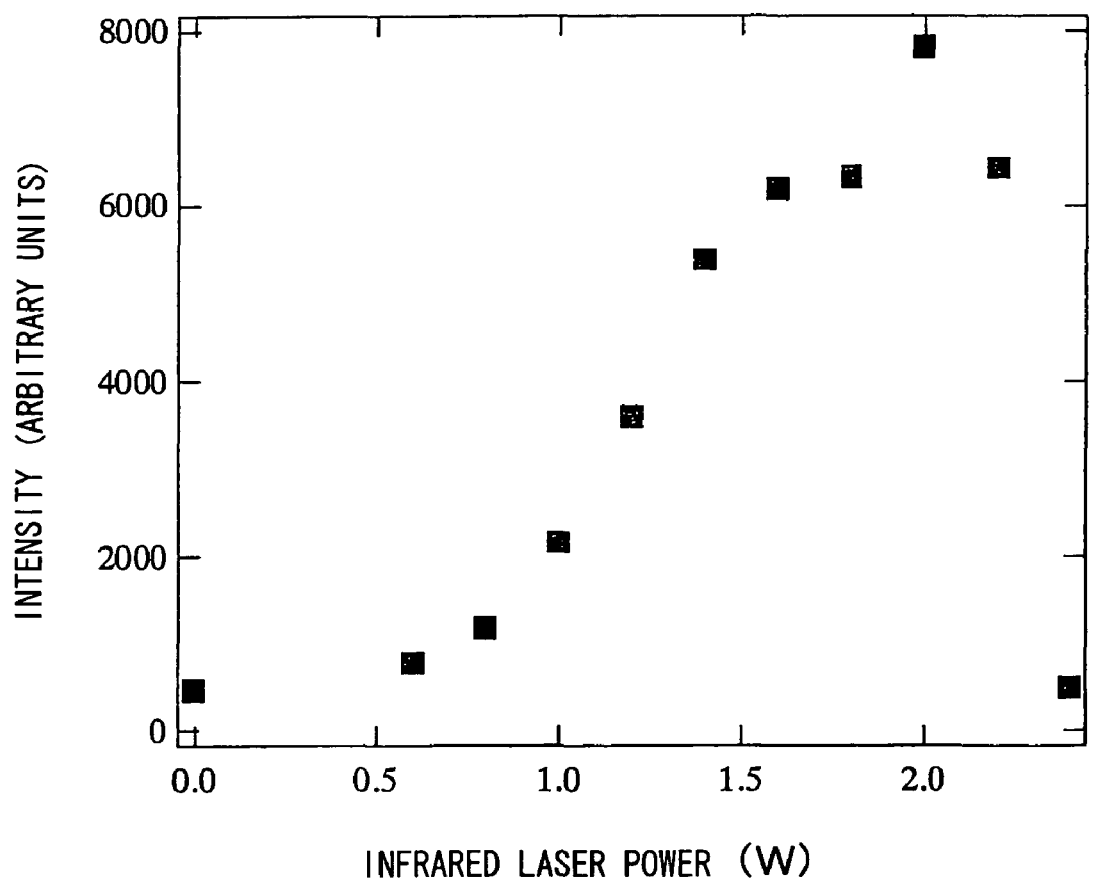
FIG. 4 is a graph illustrating a typical example of a characteristic of laser light intensity vs. ion intensity.

FIG. 4 is a graph illustrating a typical example of the dependence of ion intensity on laser intensity regarding a certain specific ion (in a case where the capillary 22 is made of stainless steel the inner and outer diameters of which are 0.1 mm and 0.2 mm, respectively, and the diameter of the laser spot is 0.3 mm). Although the intensity of the laser beam differs depending upon the type of biological sample or ions that dissociate in the biological sample, laser beam intensity vs. ion intensity is approximately as indicated by the characteristic shown in FIG. 4. When the intensity of the laser beam exceeds a certain value, ion intensity suddenly declines. The reason for this is as follows: When the sample solution that emerges from the tip of the capillary 22 is vaporized by irradiation with the laser beam, the sample solution can no longer be sprayed from the tip of the capillary 22 as electrically charged droplets because an electric field is almost entirely absent inside the stainless-steel capillary.

In order to vary infrared laser power (laser beam intensity) and detect a target ion, finding the optimum laser beam intensity is vital.

Figure 5:
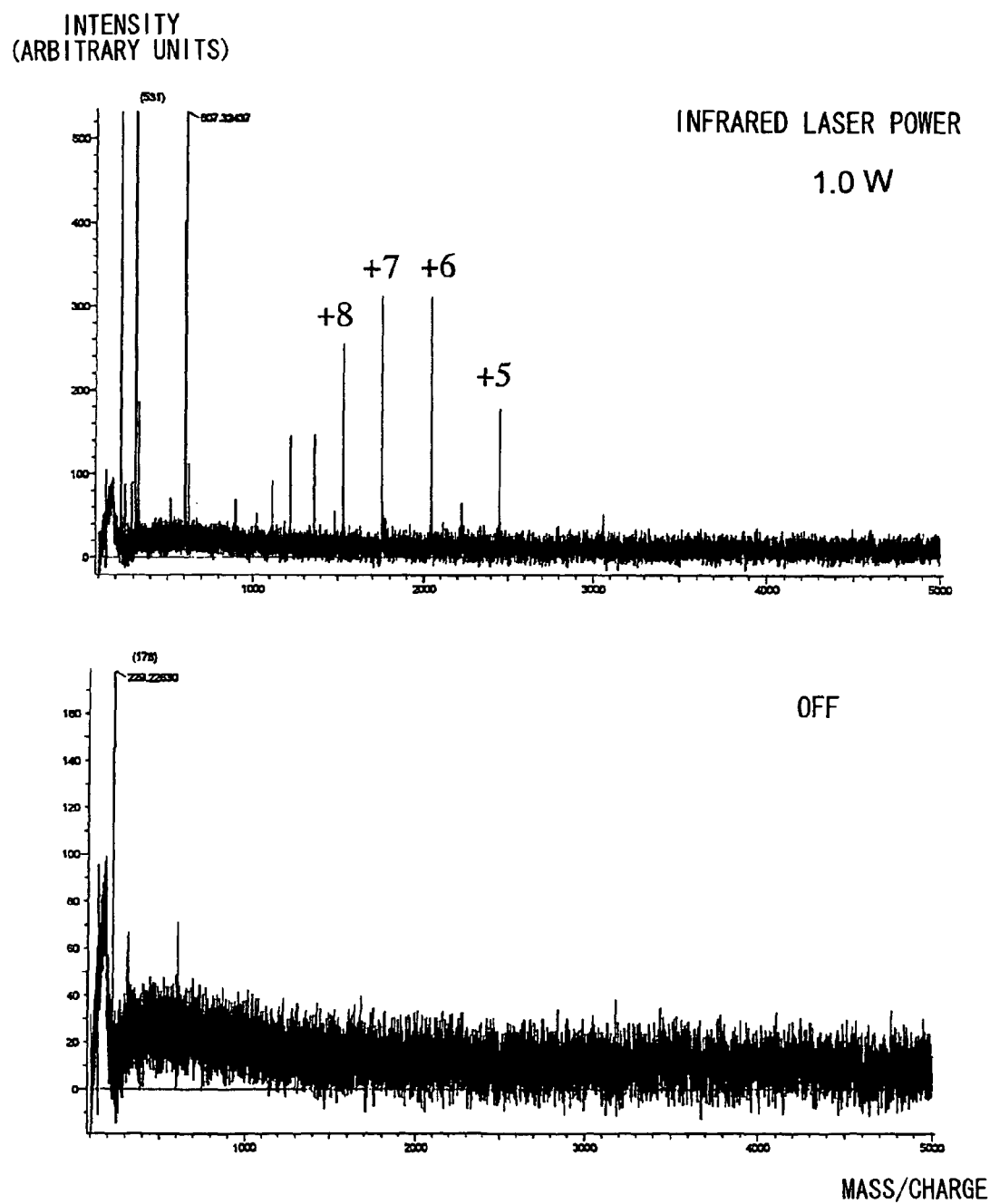
FIG. 5 illustrates mass spectra of a sample solution that contains a surface-active agent.

FIG. 5 illustrates mass spectra obtained in a case where laser power is made zero (in a case where the laser is turned off, i.e., in the electrospray mode) and in a case where laser power is made 1.0 W with regard to $10^{-5}$ M (mole) cytochrome C containing 10 mM (mol) of a surface-active agent.

In the case where the laser is turned off, only impurity ions (e.g., m/z 229.22630) are dominant.

By contrast, when irradiation is performed using the 1.0 infrared laser beam, spectra of polyvalent ions (M+nH)n+ (n=5 to 12) in which n-number of protons have been added to the cytochrome C molecule appear (m/z 607.32437 is an impurity ion).

Thus, even if a surface-active agent is present, highly sensitive detection of biological molecule (macromolecule) ions such as protein ions becomes possible by irradiation with an infrared laser beam.

Second Embodiment

Figure 6:
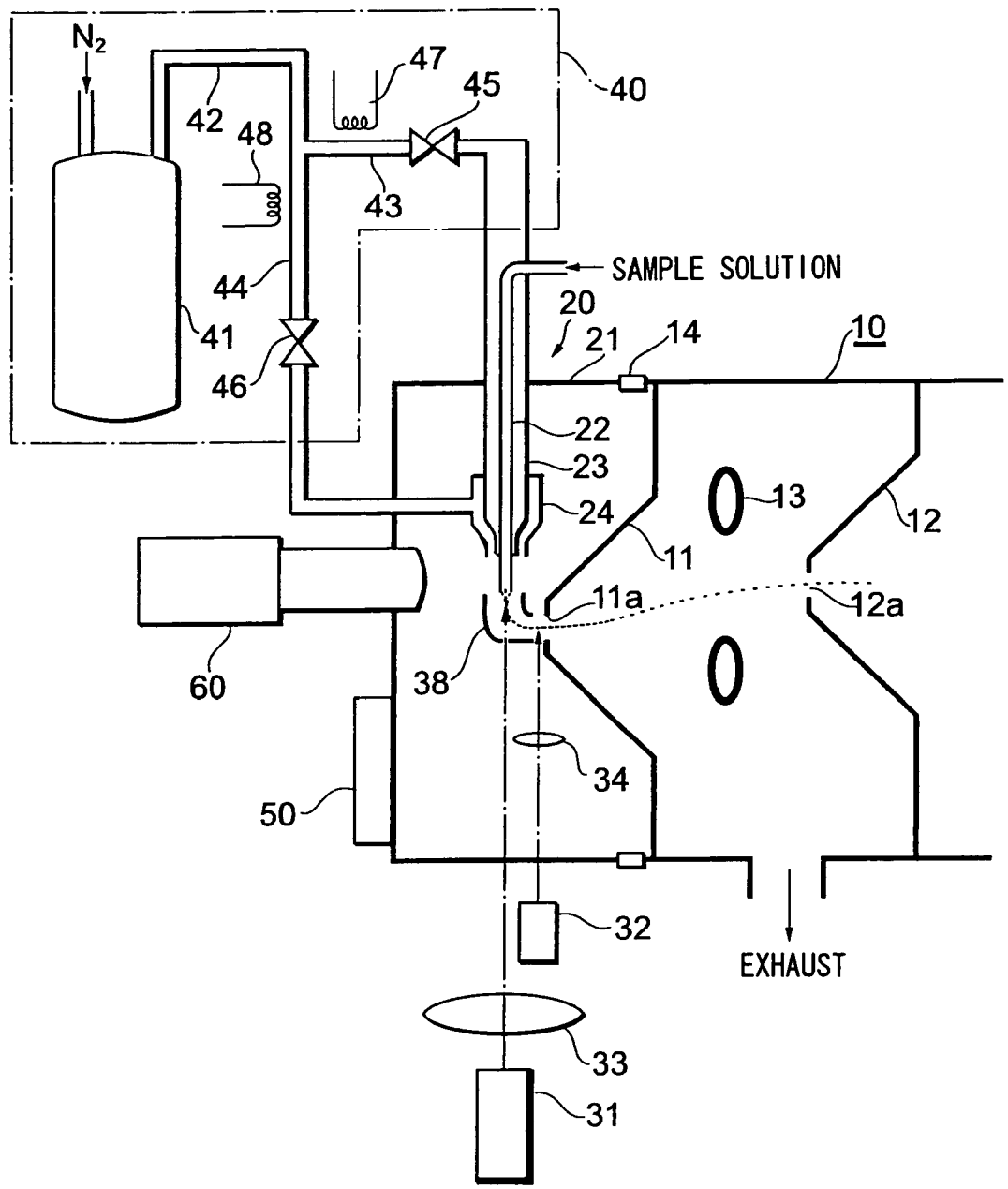
FIG. 6 is a structural view of an analyzing apparatus according to a second embodiment.

FIG. 6 is a structural view of an analyzing apparatus according to a second embodiment. Components in FIG. 6 identical with those shown in FIG. 1 are designated by like reference characters and need not be described again.

In addition to the first outer tube 23, a second outer tube 24 is provided outside the capillary 22 at the tip of the capillary 22 and spaced away from the first outer tube 23. The ends of both outer tubes 23, 24 have slender tips providing with openings in the vicinity of the tip of capillary 22.

In this embodiment, a temperature adjusting device 40 is equipped with a tank 41 of liquid nitrogen. Vaporized nitrogen gas is fed from the tank 41 to a supply tube 42. The supply tube 42 branches into two branch tubes 43, 44. The branch tubes 43, 44 are connected to the outer tubes 23, 24. The branch tubes 43, 44 are provided with flowrate regulating valves 45, 46 and heaters 47, 48, respectively, which are capable of being operated and controlled independently of one another.

The most typical method of use is to make the nitrogen gas supplied to the second outer tube 24 colder (e.g., about 0° C.) than the nitrogen gas supplied to the first outer tube 23. When the biological sample solution introduced into the capillary 22 is pre-cooled by the nitrogen gas that flows into the first outer tube 23 and the solution is sprayed from the capillary 22, the solution is cooled to a desired temperature (e.g., 0° C.) by the nitrogen gas sprayed from the second outer tube 24.

The wall of the housing 21 is provided with a Peltier element 50 and the entire interior of the ionization space (chamber) is cooled to a desired temperature.

As opposed to the foregoing arrangement, it may be so arranged that the gas supplied to the first and second outer tubes 23, 24 is made higher than room temperature to heat the sample. The same is true with regard to the ionization space. Thus, since the ionization space also has its temperature regulated, the housing 21 is attached to the vessel wall of the mass analyzer 10 via a thermal insulator 14 near the orifice 11.

A curved cylindrical guide 38 is provided for guiding the complex ions or constituent ions produced at the tip of the capillary 22 to the miniscule hole 11a of the orifice 11. The cylindrical guide 38 has a hole through which the infrared laser beam passes.

In order to observe the state of the spray of the sample at the tip of the capillary 22, a monitor 60 that includes a CCD image sensor is attached to the housing 22 so that the state at the tip of capillary 22 is imaged and displayed as a moving picture.

The laser spray apparatus of this embodiment is provided with a second laser device 32. A laser beam emitted from the second laser device 32 is focused by a lens 34 at a position on the side of the ionization space that faces the miniscule hole 11a of orifice 11.

The complex ions or constituent ions thereof produced at the tip of the capillary 22 are introduced into the mass analyzer 10 from the guide 38 through the miniscule hole 11a of orifice 11. However, immediately before the ions are introduced into the mass analyzer 10, bonds other than the aforementioned non-covalent bonds, e.g., covalent bonds of protein, are severed owing to irradiation with the second laser beam. As a result, analysis of a sequence of amino acids, for example, is possible.

It will suffice if the second laser device 32 used has a wavelength (infrared, ultraviolet or visible) suited to the type of bond to be broken.

It should be noted that in FIG. 6, the first laser beam of the first laser device 31 and the second laser beam of the second laser device 32 are illustrated as being parallel. However, this is for the convenience of illustration and it is preferred that the second laser device 32 be placed in such a manner that the second laser beam is be perpendicular to the plane of the drawing.

Third Embodiment

Figure 7:
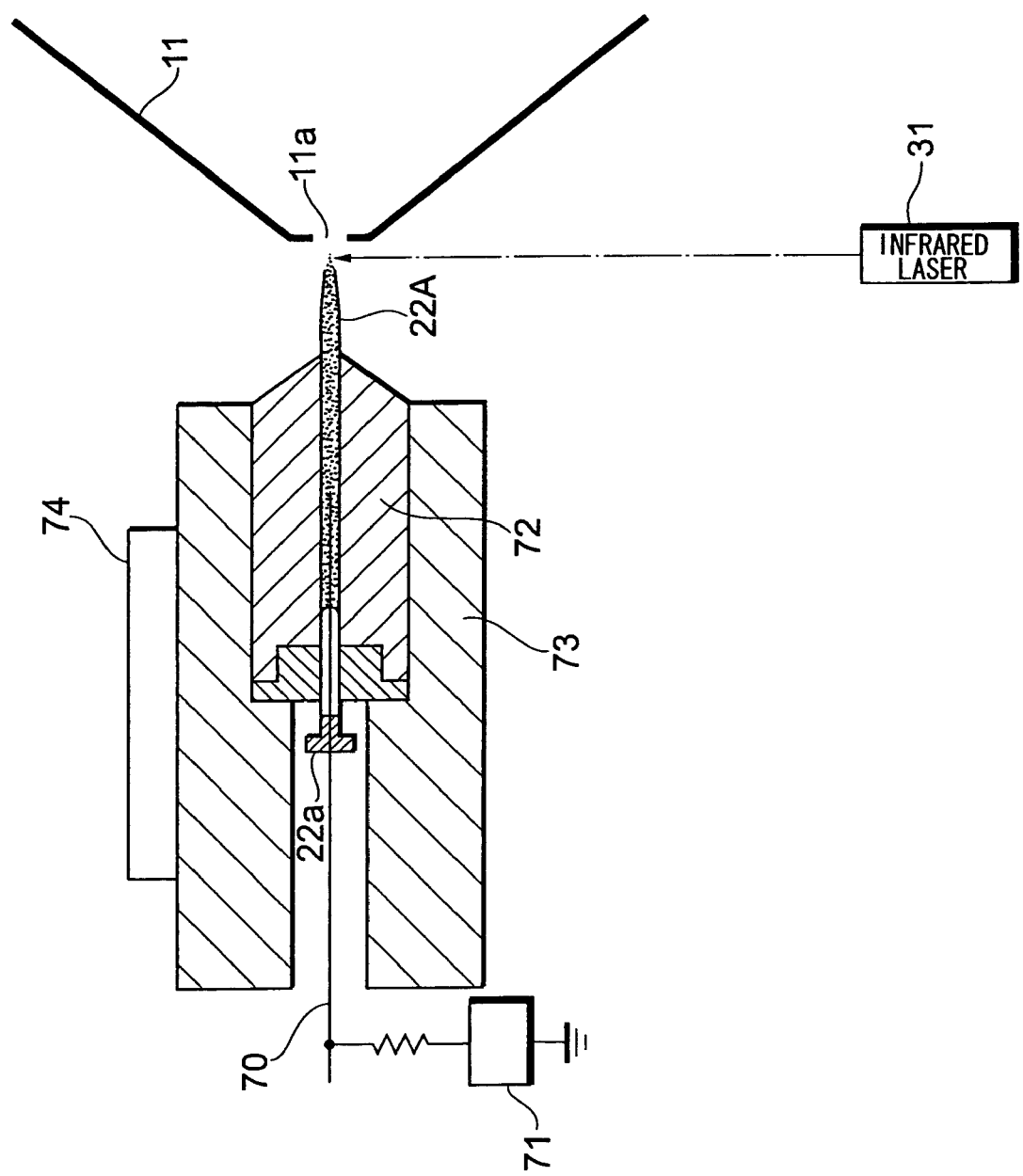
FIG. 7 is a structural view of an analyzing apparatus according to a third embodiment.

FIG. 7 illustrates a nano-laser spray apparatus.

A capillary 22A is formed from glass so as to be extremely slender, and the inner diameter of the capillary tip is on the order of 1 to 10 μm. A very small amount of the sample solution is placed in the capillary 22A and the base end thereof is closed by a plug 22a.

A metal wire (a conductor wire, typically a platinum wire) 70 is passed through the plug 22a and inserted into the capillary 22A from the base end of the capillary 22A. It will suffice if the metal wire 70 is inserted up to the vicinity of the middle of the capillary 22A along the length direction thereof. A high voltage is applied to the metal wire 70 by a high-voltage generator 71. If the metal wire 70 and sample solution within the capillary 22A are in contact, the high voltage will be applied up to the tip of the capillary through the electrically conductive sample solution. It may be so arranged that instead of inserting a metal wire, a metal membrane is vapor-deposited on the outer surface of the capillary 22A at the tip thereof and a high-voltage is applied to the metal membrane.

Owing to the high voltage applied at the tip of the capillary 22A, the sample solution is held in a state in which it protrudes from the tip of the capillary 22A. Thus the infrared laser beam from the infrared laser device 31 is emitted toward the sample solution protruding outwardly from the tip of the capillary 22A. It will suffice if the infrared laser beam does not irradiate the tip of the capillary 22A or, if it does irradiate the tip, strikes a portion at the periphery thereof.

The capillary 22A is held in a holder 72, and the holder 72 is held by a temperature regulating block 73. A Peltier element 74 is attached to the block 73 so that the temperature of the block 73 is controlled. As a result, the sample solution inside the capillary 22a is held at a desired temperature.

Figure 8:
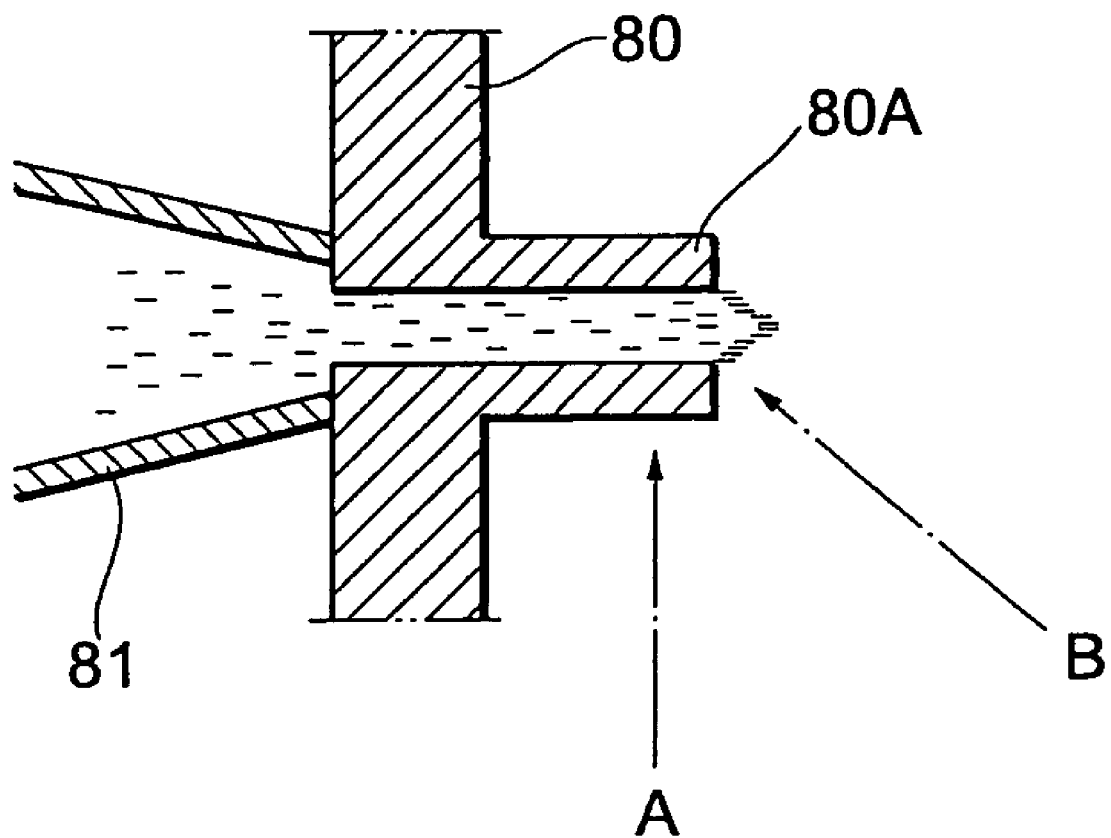
FIG. 8 is a sectional view illustrating a silicon capillary.

As illustrated in FIG. 8, one or a plurality of capillaries 80A may be formed in a silicon substrate 80 instead of using a glass capillary. The capillary 80A is an extremely slender (inner diameter on the order of 10 μm) cylindrical body formed as an integral part of the silicon substrate 80 and communicates with a hole provided in the substrate 80. The sample solution is introduced into the capillary 80A from the rear side of the substrate 80 by a slender tube 81. The capillary 80A (the tip thereof) is irradiated with the infrared laser beam from the lateral direction of the capillary 80A (the direction perpendicular to the axial direction of the capillary 80A), as indicated at A, or obliquely from the front, as indicated at B. Since silicon absorbs almost no 10.6-μm infrared light, the silicon capillary 80A will not be destroyed even if it is irradiated directly by the infrared laser beam. The tip of the silicon capillary 80A is irradiated with the infrared laser beam, the sample solution within the capillary 80A is heated and a non-covalent complex is caused to decompose. The constituents (subunit molecules) produced by decomposition experience an increase in ionization efficiency owing to the high-voltage electric field applied to the tip of the silicon capillary. It will suffice if a high-voltage is applied to the silicon substrate 80. Further, it will suffice if the silicon substrate 80 has its temperature regulated as by a Peltier element.

The invention claimed is:

1. A mass spectrometric analyzing apparatus comprising:
a capillary for supplying a sample solution;
means for forming an electric field in the vicinity of a tip of the capillary;

means for adjusting a temperature of the sample solution inside the capillary or sprayed from the capillary;

a first infrared laser light source configured to irradiate the vicinity of the tip of the capillary with an infrared laser beam; and means for introducing the sample solution sprayed from the tip of the capillary and any constituents of the sample formed upon irradiation of the sample with the infrared laser beam to a principal section of the mass spectrometric analyzing apparatus;

wherein said temperature adjusting means comprises:

a first outer tube disposed on an outer side of said capillary and spaced away from an outer peripheral surface of said capillary; and a second outer tube; which is shorter than said first outer tube, disposed in the vicinity of the tip of said capillary and spaced away from an outer side of said first outer tube;

an assist gas that has been adjusted to different temperatures being supplied to the vicinity of the tip of said capillary through respective ones of spaces between said capillary and first outer tube and between said first outer tube and said second outer tube.

2. A method of preparing a sample for mass spectrometric analysis, the method comprising:

providing a mass spectrometric analyzing apparatus, the apparatus comprising: a capillary, means for forming an electric field in the vicinity of a tip of the capillary, a first infrared laser light source; and means for introducing the sample solution sprayed from the tip of the capillary and any constituents of the sample formed upon irradiation of the sample with the infrared laser beam to a principal section of the mass spectrometric analyzing apparatus;

introducing a solution comprising a biological sample into the capillary, the biological sample comprising non-covalent complexes and having covalent bonds;

spraying the solution from a tip of the capillary under an applied electric field in the vicinity of the tip of the capillary;

irradiating at least a first portion of the solution, which flows out of a tip of the capillary under the applied electric field, with a first infrared laser beam from the first infrared laser light source to sever non-covalent bonds of at least a portion of the non-covalent complexes without severing the covalent bonds of the biological sample, thereby forming a plurality of first constituents of the biological sample; and introducing the biological sample into the principal section of the mass spectrometric apparatus for analyzing the plurality of first constituents.

3. The method according to claim 2, wherein at least a portion of the biological sample is introduced into the mass spectrometric apparatus in the form of the plurality of first constituents.

4. The method according to claim 2, wherein the mass spectrometric analyzing apparatus further comprises a second infrared laser light source; and further comprising, subsequent to irradiating at least the first portion of the solution with a first infrared laser beam, irradiating at least the first portion of the solution with a second laser beam from the second infrared laser light source to form a plurality of second constituents; wherein at least a portion of the biological sample is introduced into the mass spectrometric apparatus in the form of the plurality of second constituents.

5. The method according to claim 2, further comprising not irradiating at least a second portion of the solution, wherein at least a first portion of the biological sample is introduced into the mass spectrometric apparatus in the form of the plurality of first constituents and at least a second portion of the biological sample introduced into the mass spectrometric apparatus has not been irradiated.

6. The analyzing method according to claim 2, further comprising varying an intensity of the first infrared laser beam while irradiating the solution with the first infrared laser beam, wherein at least a portion of the biological sample is introduced into the mass spectrometric apparatus in the form of the plurality of first constituents formed by the varying the intensity of the first infrared laser beam while irradiating the solution with the first infrared laser beam.

7. The method according to claim 2, wherein the biological sample is a protein and the solution comprises a surface-active agent.

8. The method according to claim 7, further comprising cooling the biological sample inside the capillary or when sprayed.

9. The method according to claim 7, further comprising controlling a temperature of the biological sample.

* * * * *